United States Patent [19]

Minami et al.

[11] 4,101,766
[45] Jul. 18, 1978

[54] X-RAY IMAGE INTENSIFIER PHOTOFLUOROGRAPHY APPARATUS FOR CORRECTING THE BRIGHTNESS OF THE OUTPUT IMAGE

[75] Inventors: Hiroshi Minami, Yokohama; Norio Harao, Koza; Takuji Tsuneoka, Yokohama, all of Japan

[73] Assignee: Tokyo Shibaura Electric Co., Ltd., Kawasaki, Japan

[21] Appl. No.: 756,003

[22] Filed: Jan. 3, 1977

[30] Foreign Application Priority Data

Jan. 10, 1976 [JP] Japan .................................. 51-2191

[51] Int. Cl.² ............................................... G03B 5/17
[52] U.S. Cl. ..................................... 250/320; 250/510
[58] Field of Search .................. 250/320, 321, 363 R, 250/369, 510

[56] References Cited

U.S. PATENT DOCUMENTS

| | | | |
|---|---|---|---|
| 3,660,664 | 5/1972 | Pasmeg | 250/510 X |
| 3,860,817 | 1/1975 | Carmean | 250/510 X |
| 4,006,361 | 2/1977 | Schriber | 250/510 |
| 4,029,967 | 6/1977 | Tetzlaff | 250/510 X |

Primary Examiner—Davis L. Willis

Attorney, Agent, or Firm—Cushman, Darby & Cushman

[57] ABSTRACT

An X-ray image intensifier photofluorography apparatus for correcting the output image brightness while photographing an optical image of a subject in an optical camera through a lens system by amplified light into which X-rays are converted after passing from an X-ray source through the subject to an X-ray image intensifier, wherein filter means whose X-ray permeability is represented by an axially asymmetric form relative to the central horizontal axis between the X-ray source and X-ray image intensifier to correct the distribution of the intensity of X-rays emitted from the X-ray source. The X-ray permeability of the filter means is adjusted by changing a length of X-ray path or the thickness of the filter means through which X-rays are transmitted. The thickness of the filter means is determined in consideration of the distribution of the intensity of X-rays emitted from the X-ray source and the distribution of brightness of each of light images from the X-ray image intensifier and from an optical lens system. Adjustment of the distribution of the X-ray intensity by the filter means enables the light image to be photographed with a suitable brightness corresponding to the X-ray permeability of the subject on a film received in the optical camera.

8 Claims, 21 Drawing Figures (a)    (b) INTENSITY DISTRIBUTION OF AN X-RAY (a)    (b) BRIGHTNESS (a)    (b) BRIGHTNESS

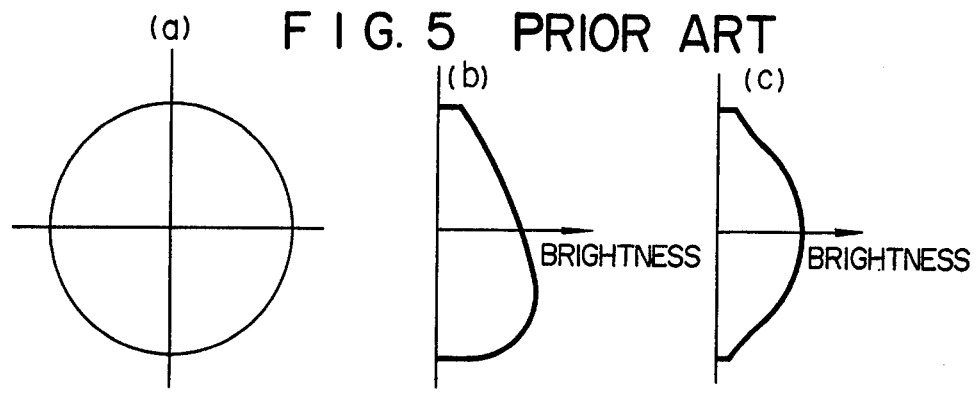
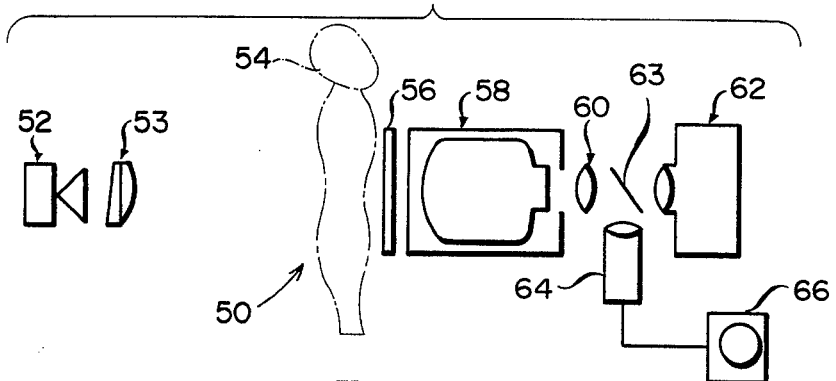
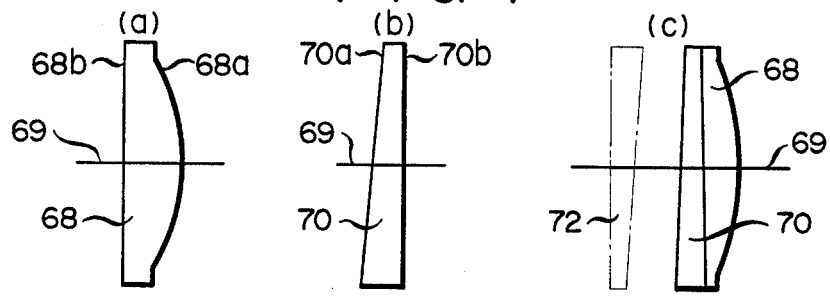
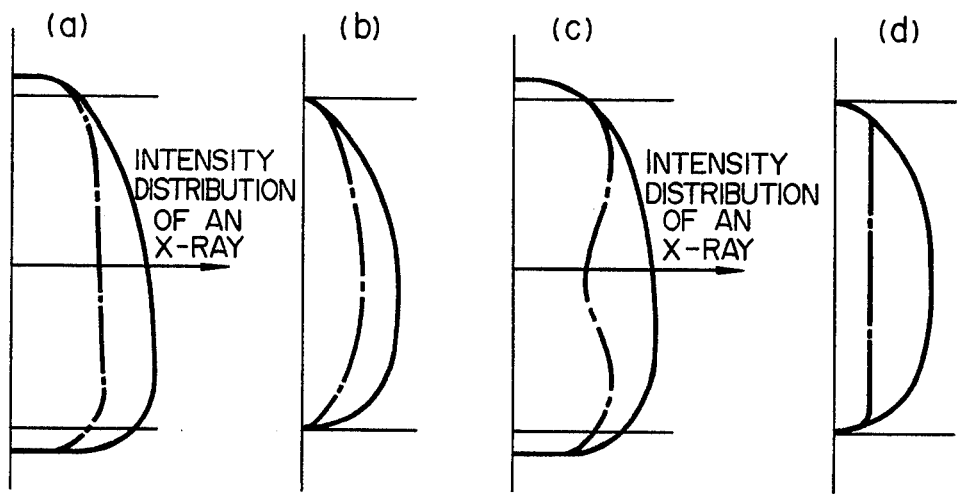

X-RAY IMAGE INTENSIFIER PHOTOFLUOROGRAPHY APPARATUS FOR CORRECTING THE BRIGHTNESS OF THE OUTPUT IMAGE

BACKGROUND OF THE INVENTION

This invention relates to an X-ray apparatus used in the field of diagnosis and more particularly to an X-ray photographing apparatus using an X-ray image intensifier and correcting the brightness of the output image.

With an X-ray photographing apparatus using an X-ray image intensifier, X-rays emitted from an X-ray source penetrate a subject to the image intensifier to be converted into visible light and to be amplified, thereby providing a light image.

With the known X-ray photographing apparatus 10 arranged as shown in FIG. 1, X-rays emitted from an X-ray source 12 are irradiated on a subject 14 and make an X-ray image of the subject 14 after passing it through. The X-ray image obtained is conducted through a grid 16 eliminating scattering X-rays and then projected to an input screen of an X-ray image intensifier 18 to be converted into a light image and to be amplified and the amplified light image are produced on an output screen. Then the light image is picked up through a lens system 20 and is focussed on a film received in an optical camera 22. An X-ray image of the subject 14 is projected on the film through the above-mentioned process. To provide an optimum X-ray photograph, the light image delivered from the lens system 20 is transferred to a television camera 24 by means of a mirror 23, thereby effecting X-ray photographing while observation is made on a television monitor 26 connected to the television camera 24. Thus, an output light image is obtained in the form of not only a film image by the aid of the optical camera 22, but also an image produced on the television monitor 26. Sometimes, an image produced on the output screen of the intensifier 18 is utilized intact through observation by an operator, instead of being conducted through the television monitor 26. However, for example, a film image obtained by the prior art X-ray photographing apparatus has the drawbacks that little light is projected on the peripheral portion of the film image due to three main causes described below, leading to a decrease in the degree of blackening on the peripheral portion and sometimes in consequence a substantial disappearance of an image from the peripheral portion.

The first cause is that the intensity of X-rays emitted from the X-ray source 12 is not uniformly distributed. As illustrated in FIG. 2a, electrons emitted from a cathode filament 29 received in the X-ray tube 28 of the X-ray source 12 impinge on an anode target 30. X-rays produced on an electron-impact surface of the anode target 30 are picked up through a radiating window 31. Since the electron-impact surface of the anode target 30 is inclined relative to the axis of the X-ray tube 28, X-rays projected on a plane parallel with the axis do not present an axially symmetric intensity distribution relative to a perpendicular from the focus of the anode target 30 to the projection plane. Namely the intensity of X-rays is distributed such that it is maximum in the direction perpendicular to the surface of the anode target and minimum or zero in the direction tangential to the surface thereof. Generally, X-rays have an intensity inversely proportional to a distance through which they travel. Therefore, X-rays passing through by the peripheral portion of the radiating window 31 travel for a longer distance than those conducted through the central portion of the radiating window 31 and in consequence decrease in intensity on the projection plane than the X-rays which are emitted through the central portion. As the result, X-rays vertically thrown on the projection plane present an intensity distribution represented as the solid line, as shown in FIG. 2b, by an asymmetric curve which becomes extremely small on one side of the curve and most prominent in a region defined between the other side and central portion of the curve. While X-rays horizontally thrown on the projection plane present an intensity distribution represented as the dot line.

The second cause leading to the non-uniform brightness of a film image is that X-rays attenuate spatially unevenly in the intensifier 18. Even when X-rays initially having the uniform intensity distribution enter the intensifier 18, an output light image therefrom does not indicate a uniformly distributed brightness. Now let it be assumed that X-rays 33a, 33b having the same intensity are brought into the intensifier 18 from the X-ray source 12. X-rays entering a tube envelope 34 of the intensifier 18 pass to an input screen 36 through a face plate 35. X-rays conducted through an aluminium base plate 36a reach a fluorescent layer 36b to be converted into light therein. X-rays 33b obliquely entering the intensifier 18 travel a longer distance to the face plate 35 than X-rays 33a entering the face plate 35 at right angles and also have to run a longer distance through the face plate 35 than the latter X-rays 33a. Therefore, the X-rays 33b are more attenuated and have a lower intensity than the X-rays 33a. Moreover, the X-rays 33b obliquely entering the fluorescent layer 36b present a longer fluorescent length with the resultant decline in the degree of resolution. Nevertheless, an attempt progressively to reduce the thickness of the fluorescent layer 36b from the center toward the periphery in order to unify the fluorescent lengths produced by X-rays would decrease the X-rays to light conversion efficiency. Further, due to the distortion an output light image appearing on an output screen 38 takes the pincushion distortion whose peripheral portions are larger than the central portion. Therefore, an amount of light per unit area in the peripheral portions of the output light image is smaller than in the central portion thereof, indicating a relatively lower brightness. For the above-described reason, an output light image presented on the output screen 38 of the intensifier 18 has a non-uniform brightness, namely, as shown in FIG. 5b, the brightness reaches a maximum level in the central portion of the output screen 38 and indicates a minimum level represented by an axially symmetric curve in the peripheral portions of the output screen 38. The brightness in the peripheral portions accounts for about 60% of that of the central portion.

The third cause giving rise to the uneven brightness of an output light image projected on a film is that the image focussed by the lens system 20 itself has a non-uniform brightness. As seen in FIG. 4a, the lens system 20 generally comprises a pair of convex lenses 40, 41. The forward lens 40 converts light from the intensifier 18 into parallel light, and the rear lens 41 focus the parallel light. Light starting from the central point 43a of the light image 43 goes straight to the central point 44a of the focussed image 44. Light sent forth from the upper point 43b of the light image 43 is projected on the lower point 44b of the focussed image 44. Light from the central point 43a of the light image 43 is introduced at an angle falling within the range of a solid angle α, whereas light from the upper point 43b of the light image 43 is supplied at an angle falling within the range of a solid angle β. Since the solid angle β is smaller than the solid angle α and the central line thereof is inclined, light emitted from the upper point 43b of the light image 43 has a smaller amount than light emitted from the central point 43a thereof. When converted into a parallel form by the forward lens 40, light from the upper point 43b is not rendered fully parallel with the optical axis of the forward lens 40. Namely, a bundle of the parallel light from the upper point 43b is slightly inclined as a whole from the optical axis of the forward lens 40. Part of the light is displaced from the rear lens 41 and does not contribute to the convergence of light from the light image 43 at the lower point 44b of the focussed image 44. This event also arises with respect to light emitted from the lower point 43b of the light image 43. As shown in FIG. 4b, therefore, light occupying the peripheral portions of a light image focussed by the lens system 20 has a smaller amount than those of the central portion of the focussed image. As the result, the brightness of the focussed light image has a distribution axially symmetrical with respect to the axis of the image.

The above-mentioned three causes collectively give rise to a considerable decrease in an amount of light lying in the peripheral portions of a light image projected on a film received in the optical camera from that of light occupying the central portion of the light image. Where an X-ray tube is set upright, as shown in FIG. 2 and the target 30 is positioned above the cathode filament 29, a circular light image indicated in FIG. 5a has a brightness in the vertical direction which is distributed as shown in FIG. 5b and a brightness in the horizontal direction which is distributed as indicated in FIG. 5c. The brightness of the light image in the vertical direction has a distribution represented by axially asymmetric curve in which a maximum brightness appears in a region defined between one end and the center of the light image. The brightness of the light image in the horizontal direction has a distribution denoted by an axially symmetric curve in which a maximum brightness is presented in the central portion of the light image.

The foregoing description refers to an output light image projected on a film. Neither of an output light image from the intensifier 18 and an output light image from the television monitor 26 fails to have a uniform brightness from the effect of the X-ray source 12 and intensifier 18, to say nothing of the effect of the optical camera.

Various attempts have hitherto been made to eliminate drawbacks accompanying the prior art X-ray photographing apparatus. One of the known X-ray photographing apparatuses is the type in which a glass face plate 35 has its thickness increased in the central portion and progressively reduced toward the periphery to cause X-rays to be attenuated at a uniform rate. With this apparatus, however, it is necessary to emit a larger dosage of X-rays in order to produce a light image having a uniform brightness. Where a subject 14 is a human body, and, for example, his stomach is photographed by X-rays, application of an increased dosage of X-rays very adversely affects the human body, for example, exerts a harmful effect on a gene or gives rise to the more frequent occurrence of leukemia. Further, increased dosage of X-rays results on a larger absorption of X-rays in the central portion of the inlet screen 36, and more prominent scattering of X-rays, thereby causing a light image to present a less distinct contrast of an output image. Another prior art X-ray photographing apparatus is the type wherein a metal back of the output screen of the intensifier 18 which is formed by vacuum deposition of an aluminum layer has its thickness increased at the center, thereby purposely causing the brightness of a light image to be progressively decreased toward the center of the light image. In this case, too, in comparison with the known apparatus having an aluminium layer where thickness is uniform, X-rays must be applied profusely, with the resultant drawback that the central portion of the input screen 36 becomes unduly bright, leading to an increase in an amount of reflected light at the input screen and the adjacent area thereof and in consequence a less distinct contrast in the light image.

With still another conventional X-ray photographing apparatus, a mask bored with a smaller hole than the diameter of a forward lens 40 is provided as an iris diaphragm between the forward and rear lenses 40, 41 in order to prevent an amount of light from being reduced in the periphery of a light image delivered from the lens system 20. This arrangement can indeed provide a focussed image having a uniform brightness by cutting off the peripheral portions of a bundle of parallel light passing through the forward lens 40. But removal of the peripheral portion of the bundle of parallel light decreases an amount of light taking part in providing a focussed image. Therefore, this prior art X-ray photographing apparatus is still accompanied with the drawback that an increased dosage of X-rays has to be applied in order to obtain a fully bright focussed image.

SUMMARY OF THE INVENTION

It is accordingly the object of this invention to provide an X-ray photographing apparatus capable of producing an output image of a subject with a suitable brightness without applying an increased dosage of X-rays or reducing a contrast of the image.

To attain the above-mentioned object, in one preferred embodiment, this invention provides an X-ray photographing apparatus wherein X-ray distribution-correcting filter means for correcting the distribution of X-rays whose attenuation rate corresponds to the distribution of the brightness of a light image projected on a film received in an optical camera is provided between an X-ray source and X-ray image intensifier. The filter means comprises a wedge-like filter, one side of which is inclined crosswise relative to the central line and the other side of which intersects the central line at right angles and another filter, one side of which takes an arciform and the other side of which intersects the central line at right angles. Both filters are fixed in place, shown as in FIG. 6, such that the flat planes of the wedge-like filter and the arciform filter face each other.

The X-ray photographing apparatus of this invention uses the arciform filter whose surface changes in form and the wedge-like filter whose inclined plane varies in the angle of inclination, both according to the distribution of the brightness of a light image which would be projected on an X-ray photographing film in the absence of the filter means. X-rays passing through the above mentioned composite filter means having a non-uniform thickness as a whole present different attenuation rates according to the those parts of the filter means through which the X-rays are transmitted, eventually providing a light image having a uniform distribution of brightness.

Other objects, features and advantages of this invention will become apparent as the description thereof proceeds when considered in connection with the accompanying drawings.

BRIEF DESCRIPTION OF THE DRAWING

FIGS. 1 to 5 illustrate the prior art X-ray photographing apparatus.

FIGS. 6 to 11 show the X-ray photographing apparatus of this invention.

FIG. 1 is a schematic front view of the prior art X-ray photographing apparatus;

FIG. 2a shows the manner in which X-rays are emitted from the anode target of an X-ray tube of a X-ray source used with the prior art X-ray photographing apparatus of FIG. 1;

FIG. 2b indicates the distribution of the intensity of X-rays;

FIG. 3a is a schematic front view of X-ray image intensifier used with the prior art X-ray photographing apparatus of FIG. 1;

FIG. 3b presents the distribution of the brightness of a light image sent forth from the X-ray image intensifier;

FIG. 4a is a front view of a lens system used with the prior art X-ray photographing apparatus of FIG. 1;

FIG. 4b shows the distribution of the brightness of a light image delivered from the lens system;

FIG. 5a illustrates the manner in which a light image is focussed by the lens system;

FIG. 5b indicates the distribution of the brightness of a focussed light image in the vertical direction;

FIG. 5c sets forth the distribution of the brightness of the focussed light image in the horizontal direction;

FIG. 6 is a schematic front view of an X-ray photographing apparatus embodying this invention;

FIGS. 7a to 7c are front views of filters constituting filter means used with the X-ray photographing apparatus of FIG. 6 according to this invention;

FIG. 8a to 8d present the manner in which the distribution of the brightness of a light image is corrected by the filter means of this invention;

FIGS. 9 and 10 illustrate the arrangement of the filter means when X-ray photographing is undertaken in the magnified form; and FIG. 11 shows the arrangement of the filter means when the view field of the X-ray image intensifier is changed.

DETAILED DESCRIPTION OF THE PREFERRED EMBODIMENTS

Figure 1:
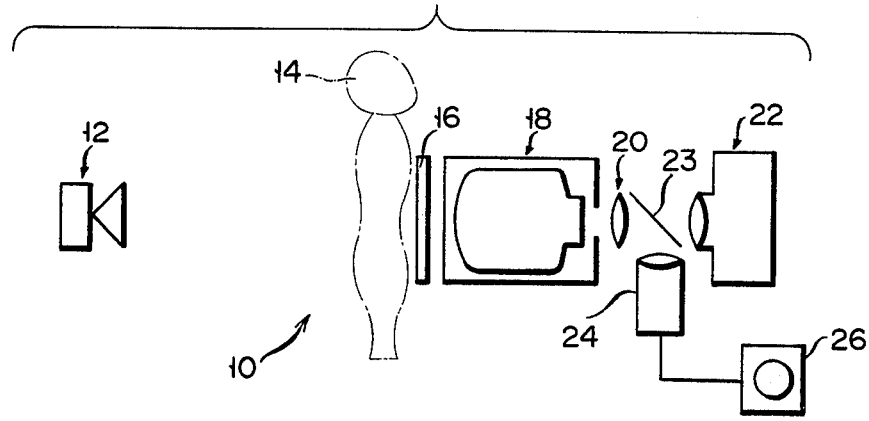
Figure 2:
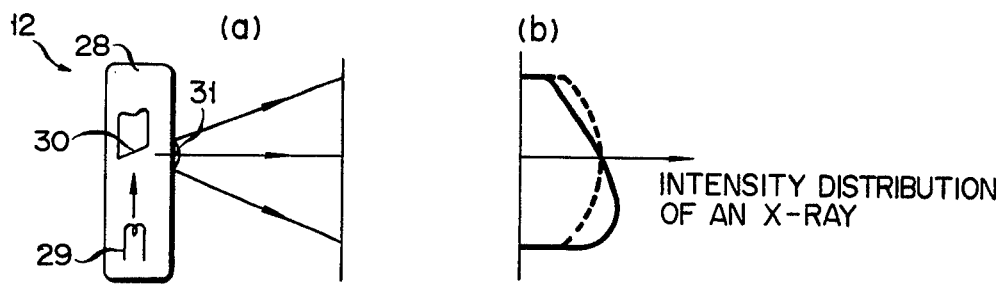
Figure 3:
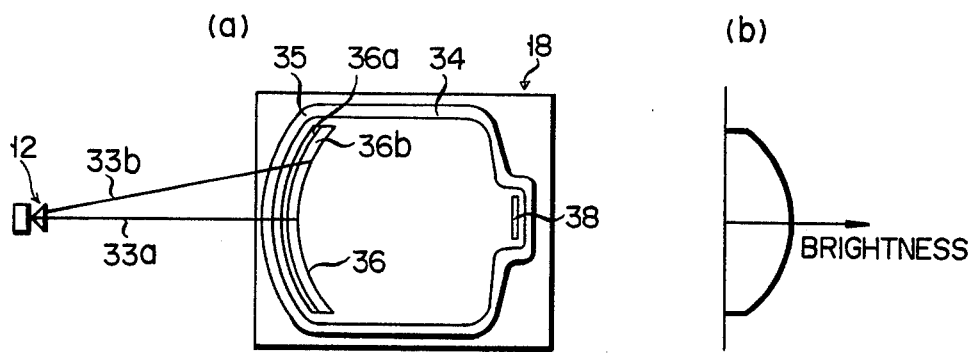
Figure 4:
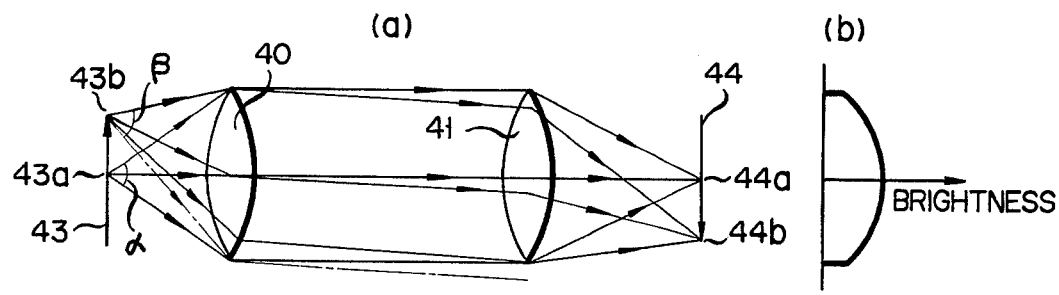

Referring to FIG. 6, an X-ray photographing apparatus 50 embodying this invention is provided with filter means 53 which is adapted to correct the distribution of X-rays, and disposed between an X-ray source 52 and X-ray image intensifier 56 and whose thickness or cross section has such an outline as is axially asymmetric relative to the horizontal axis of a central line between the X-ray source and X-ray image intensifier. X-rays emitted from the X-ray source 52 are properly corrected in the distribution of intensity while passing through the filter means 53 having a non-uniform thickness and in consequence causing X-rays to be attenuated at different rates according to the points through which the X-rays are transmitted. X-rays whose intensity distribution has now been corrected penetrate a subject 54 to form an X-ray image. And various substances constituting the subject 54 have their own X-ray permeabilities and thus, lead intensity distribution of penetrated X-rays to correspond to the distribution of the substances. Namely the intensity of the penetrated X-rays is spatially modulated. Scattering X-rays occurring at this time are eliminated by a grid 56. Proper streams of X-rays stripped of the scattering portions enter an intensifier 58. The X-ray image is converted into amplified light which in turn is projected on a film received in an optical camera 62. For optimum photographing in the optical camera 62, the light is transferred from the lens system 60 to a television camera 64 by means of mirror 63 to be monitored by a monitor 66.

With the X-ray photographing apparatus of this invention, X-rays are corrected in the distribution of intensity by passing through the filter means 53 whose thickness or cross section has such an outline as is axially asymmetric relative to the horizontal axis between the X-ray source 52 and the intensifier 58, namely, has a maximum area between one end and central portion, thereby easily providing a light image having a uniform brightness. Further advantages of this invention are that it is unnecessary to apply an increased dosage of X-rays to the subject 54 as is the case with the prior art X-ray photographing apparatus, excessive scattering of X-rays is prevented, reduction of a contrast of an output image caused by emission of light from the input fluorescent layer of the intensifier 58 due to the excessive scattering of X-rays can be minimized, and the filter means 53 has a suitable thickness distribution to present a desired X-ray permeability, making it possible to correct the distribution of the brightness of an output image up to an optimum level.

FIGS. 7a and 7b show the component filters of the filter means 53 for correcting the distribution of X-rays. The component arciform filter 68 shown in FIG. 7a has a curved surface 68a which projects outward at the center and indicates an axially symmetric outline relative to the horizontal axis 69, and a straight surface 68b which intersects the horizontal axis at right angles. The filter means 68 may be formed of aluminium so as to cause the central thickness to be 3 mm and the peripheral thickness to be 0.5 mm. From the standpoint of working, the curved surface 68a may be allowed to approximate a spherical surface. This arciform filter 68 is effective to correct the distribution of the brightness of a light image issued from the intensifier 58 and lens system 60 in which the brightness of a light image has such a distribution as indicates an axially symmetric outline relative to the horizontal axis.

A filter 70 having a wedge-like cross section as shown in FIG. 7b has one inclined surface 70a and a straight surface 70b intersecting the horizontal axis at right angles. The wedge-like filter 70 may be formed of, for example, aluminium so as to have a maximum thickness of 3 mm, a minimum thickness of 0.5 mm as viewed in the axial direction and a suitable height. However, the thickness of the wedge-like filter 70 does not change in the width direction. The wedge-like filter 70 is effective to unify the distribution of the intensity of X-rays emitted from the X-ray source 52. The wedge-like filter 70 serves the purpose, provided its thickness varies only in one direction. From the standpoint of working, the wege-like filter 70 simply has an inclined plane 70a.

The component filters 68, 70 of the filter means 53 are so worked as to have different thickness distribution according to the quality of X-rays applied. In practice, the above-mentioned two filters 68, 70 are jointly used to correct all effects on output images from the X-ray source 52, intensifier 58 and lens system 60. Both filters 68, 70 may be applied in an integral form by fixing together the straight planes 68b, 70b as shown in FIG. 7c, or separately. Further, it is possible to use another wedge-like filter 72 having a vertically opposite tapered form to the aforesaid wedge-like filter 70 at a prescribed distance from the integrally coupled filters 68, 70. This arrangement causes X-rays to be attenuated at a complicated rate. Where X-rays have a tendency to present a prominent asymmetric distribution of intensity, then it is advised to set the additional wedge-like filter 72 with the pointed portion thereof aligned with that of the other wedge-like filter 70. Further, the additional wedge-like filter 72 may obviously be integrated with the other two filters 68, 70.

If formed of a metal such as copper, iron or, lead which has a lower X-ray permeability than aluminum, the filters 68, 70, 72 can be considerably reduced in thickness. A filter made of other metals than aluminum may be formed by vacuum evaporation, but has the disadvantage of presenting difficulties in working due to small variations in thickness. Therefore, it is advaised properly to select the material of the filter according to its dimension required for practical application. It is possible to prepare the filter from nonmetallic material such as ceramics which admits of easy working.

Figure 9:
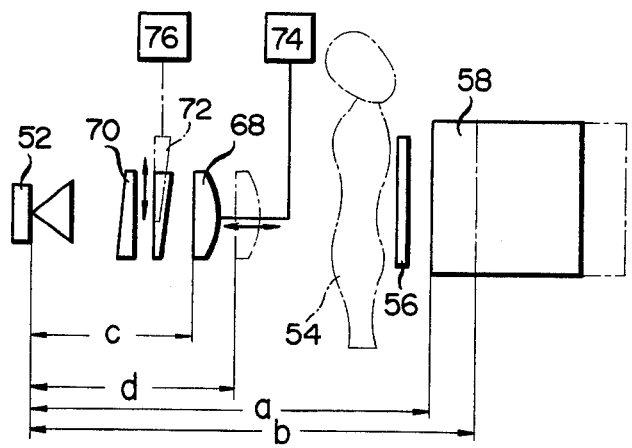

FIGS. 8a to 8d show the corrected intensity distribution of X-rays. Throughout these figures, a solid line denotes the case where the filter means of this invention was not used. An one-dot chain line represents the case where the filter means of the invention was applied. FIG. 8a presents the intensity distribution of X-rays when the wedge-like filter 70 alone was used and FIG. 8c indicates the intensity distribution of X-rays when the integrally coupled filters 68, 70 were applied. FIGS. 8b and 8d set forth the distributions of the brightness of a light image projected on an X-ray photographic film when the wedge-like filter 70, and the integrally coupled arciform filter 68 and wedge-like filter 70 were used respectively. As seen from FIGS. 8a and 8b, application of the wedge-like filter 70 alone failed to cause a light image to have a uniform distribution of brightness, though allowing X-rays to present a uniform distribution of intensity. In contrast, where the arciform filter 68 and wedge-like filter 70 were jointly used, X-rays indicated such distribution of intensity as decreased at the central portion, as apparent from FIGS. 8c and 8d. X-rays which indicate a more noticeable attenuation rate at the periphery of a light image than at the center thereof due to the effect from the intensifier 58 and lens system 60 eventually enable to light image having a uniform brightness to be projected on the X-ray photographic film. The intensity distribution of X-rays is corrected by the filters 68, 70 under the attenuated condition of X-rays at the center of a light image.

Where the intensifier 58 is removed from the subject 54, namely, from the X-ray source 52 for magnified X-ray photographing, it is impossible to carry out the required correction of the intensity distribution of X-rays, unless the position of the filter means 53 is also changed. Where, as shown in FIG. 9, the intensifier 58 spaced from the X-ray source 52 at a distance "a" is shifted to a point spaced from the X-ray source 52 at a distance "b," then it is necessary to shift the arciform filter 68 spaced from the X-ray source 52 at a distance "c" to a point spaced from the source at a distance "d" according to changes in a distance between the intensifier 58 and X-ray source 52. The distance "d" may be expressed by an equation $d = (b/a)c$. Referential numeral 74 denotes drive means for transporting the arciform filter 68 in the axial direction. The above-mentioned operation is not limited to the arciform filter 68. But shifting any of the filters 68, 70, 72 obviously attains desirable magnified X-ray photographing. If the wedge-like filter 72 is designed to be vertically moved relative to the axis by drive means 76, then it is possible to correct the distribution of the intensity of X-rays at a more complicated rate.

Figure 10:
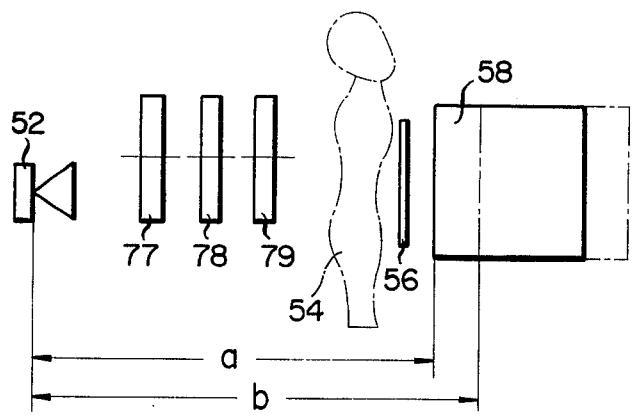
Figure 11:
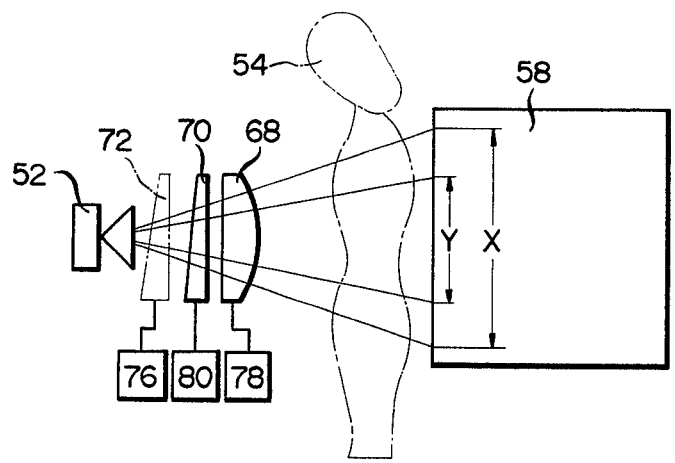

If the filters 68, 70, 72 are replaced by turrets 77, 78, 79 fitted with various types of filters as shown in FIG. 10, then it is possible to use filters in an optimum combination, if the turrets 77, 78, 79 are selectively revolved in accordance with the distance through which the intensifier 58 is shifted. Application of the turrets admits of the effective utilization of a space between the X-ray source 52 and intensifier 58. It is possible to provide only one turret in place of the arciform filter 68 instead of using three turrets. Further, the filters 68, 70, 72 may be interchangeably used by manual operation or by automatic remote control.

Where the view field of the intensifier 58 is changed from X to Y as shown in FIG. 11, it is possible to eliminate the filter 68 for connecting the effect of the intensifier 58, because a light image appearing the view field Y presents very small differences in brightness.

Since the sensitivity of the intensifier 58 considerably falls in the case where the view field thereof is thus reduced, it is preferred to remove the filter 68 in order to decrease a load on the X-ray source 52. Further, it is advised vertically to shift the filter 68 by the drive means 74 according to the manner in which the view field of the intensifier 58 is changed. Where X-rays present a substantially axially symmetric distribution of intensity regardless of the view field of the intensifier 58, then the wedge-like filter 70 should preferably be removed by drive means 82. Where X-rays indicate a prominent linearly asymmetric distribution of intensity, then it is advised to insert the wedge-like filter 72 by drive means 76. To minimize the exposure of a subject to scattering X-rays, it is desired to remove the filter means from the subject as far as possible. This invention is not limited to the above-mentioned embodiment, but can be applied in various modifications without departing from the technical scope and idea of the invention as hereinafter claimed.

What we claim is:

1. An X-ray image intensifier photofluorography apparatus for emitting X-rays from an X-ray source through a subject to an X-ray image intensifier, converting the X-rays into amplified light, photographing the light image through a lens system in an optical camera, and correcting the brightness of the output image, wherein X-ray distribution-correcting filter means whose X-ray permeability is represented by an axially asymmetric form relative to the horizontal axis is disposed between the X-ray source and X-ray image intensifier.

2. The X-ray photographing apparatus according to claim 1, wherein the X-ray distribution-correcting filter means comprises a first filter whose thickness is so distributed as to be thick at the center and thin at both ends, and at least one second filter whose thickness is so distributed as to be thick at one end and progressively thinner toward the other end and does not change in the width direction.

3. The X-ray photographing apparatus according to claim 2, wherein the first filter is an arciform type, one side of which takes a substantially spherical form most projecting outward at the center, and the second filter is a wedge-like type, one side of which is inclined toward one end.

4. The X-ray photographing apparatus according to claim 3, wherein each of the other sides of the spherical filter, and the wedge-like filter is a plane intersecting the horizontal axis at right angles.

5. The X-ray photographing apparatus according to claim 2, wherein the X-ray image intensifier is spaced from the X-ray source at a prescribed distance, and the first and second filters are integrally coupled, the second filter being provided in a single number.

6. The X-ray photographing apparatus according to claim 2, wherein the X-ray source and X-ray image intensifier are spaced from each other at a variable distance, the first and second filters are separately provided, and either of both filters is shifted in the horizontal axial direction according to a varied distance between the X-ray source and X-ray image intensifier.

7. The X-ray photographing apparatus according to claim 2, wherein the X-ray source and X-ray image intensifier are spaced from each other at a variable distance, two second filters are provided, the first filter and the second filters are separately disposed, and either of the two second filters is moved in a direction perpendicular to the horizontal axis according to a varied distance between the X-ray source and X-ray image intensifier.

8. The X-ray photographing apparatus according to claim 2, wherein the X-ray source and X-ray image intensifier are spaced from each other at a variable distance, the first and second filters are separately provided, and either of the first and second filters is fitted to a turret which is rotated to an extent corresponding to a varied distance between the X-ray source and X-ray image intensifier.

* * * * *